United States Patent [19]
Beckett et al.

[11] Patent Number: 5,866,717
[45] Date of Patent: Feb. 2, 1999

[54] METALLOPROTEINASE INHIBITORS

[75] Inventors: Raymond Paul Beckett; Mark Whittaker; Andrew Miller; Fionna Mitchell Martin, all of Oxford, United Kingdom

[73] Assignee: British Biotech Pharmaceuticals Limited, Oxford, England

[21] Appl. No.: 836,839

[22] PCT Filed: Nov. 27, 1995

[86] PCT No.: PCT/GB95/02770

§ 371 Date: May 21, 1997

§ 102(e) Date: May 21, 1997

[87] PCT Pub. No.: WO96/16931

PCT Pub. Date: Jun. 6, 1996

[30] Foreign Application Priority Data

Nov. 26, 1994 [GB] United Kingdom ............ 9423914

[51] Int. Cl.⁶ ............ C07C 235/70; C07D 333/32
[52] U.S. Cl. ............ 623/523; 562/621; 549/65
[58] Field of Search ............ 562/621, 623; 549/65

[56] References Cited

U.S. PATENT DOCUMENTS

| | | |
|---|---|---|
| 3,468,936 | 9/1969 | van der Burg . |
| 4,599,361 | 7/1986 | Dickens et al. . |
| 4,996,358 | 2/1991 | Handa et al. ............ 562/621 |
| 5,183,900 | 2/1993 | Galardy et al. . |
| 5,256,657 | 10/1993 | Singh et al. . |
| 5,270,326 | 12/1993 | Galardy et al. . |
| 5,300,501 | 4/1994 | Porter et al. ............ 514/238.2 |
| 5,300,674 | 4/1994 | Crimmin et al. . |
| 5,304,549 | 4/1994 | Broadhurst et al. . |
| 5,569,665 | 10/1996 | Porter et al. ............ 514/357 |
| 5,643,964 | 7/1997 | Dickens et al. . |

FOREIGN PATENT DOCUMENTS

| | | |
|---|---|---|
| 0231081 | 8/1987 | European Pat. Off. . |
| 0274453 | 7/1988 | European Pat. Off. . |
| 0489577 | 6/1992 | European Pat. Off. . |
| 0489579 | 6/1992 | European Pat. Off. . |
| 0497192 | 8/1992 | European Pat. Off. . |
| 0574758 | 12/1993 | European Pat. Off. . |
| 0575844 | 12/1993 | European Pat. Off. . |
| 9005716 | 5/1990 | WIPO . |
| 9005719 | 5/1990 | WIPO . |
| 9102716 | 3/1991 | WIPO . |
| 9209563 | 6/1992 | WIPO . |
| 9213831 | 8/1992 | WIPO . |
| 9217460 | 10/1992 | WIPO . |
| 9222523 | 12/1992 | WIPO . |
| 9309090 | 5/1993 | WIPO . |
| 9309097 | 5/1993 | WIPO . |
| 9320047 | 10/1993 | WIPO . |
| 9324449 | 12/1993 | WIPO . |
| 9324475 | 12/1993 | WIPO . |
| 9402446 | 2/1994 | WIPO . |
| 9402447 | 2/1994 | WIPO . |
| 9410990 | 5/1994 | WIPO . |
| 9421612 | 9/1994 | WIPO . |
| 9421625 | 9/1994 | WIPO . |
| 9424140 | 10/1994 | WIPO . |
| 9425434 | 11/1994 | WIPO . |
| 9425435 | 11/1994 | WIPO . |
| 9519961 | 7/1995 | WIPO . |

OTHER PUBLICATIONS

Conway et al, *The Journal of Experimental Medicine*, vol. 182, pp. 449–457, Aug. 1995.

DiMartino et al, *Annals of the New York Academy of Sciences*, vol. 732, pp. 411–413, 1994.

Gijbels et al, *J. Clin. Invest.*, vol. 94, No. 6, pp. 2177–2182, Dec. 1994.

*Primary Examiner*—Gary Geist
*Assistant Examiner*—Brian J. Davis
*Attorney, Agent, or Firm*—Hale and Dorr LLP

[57] ABSTRACT

Compounds of general formula (I), principally characterized in that R4 is a polyether group, are water soluble matrix metalloproteinase inhibitors.

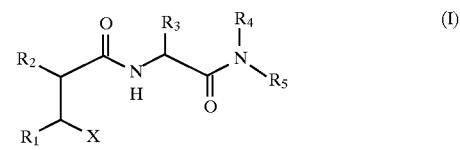

13 Claims, No Drawings

METALLOPROTEINASE INHIBITORS

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteinases involved in tissue degradation, and in addition are inhibitors of the release of tumour necrosis factor from cells.

BACKGROUND TO THE INVENTION

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ion at the active site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. Chapman et al J. Med. Chem. 1993, 36, 4293–4301 report some general structure/activity findings in a series of N-carboxyalkyl peptides. Other known MMP inhibitors are less peptidic in structure, and may more properly be viewed as pseudopeptides or peptide mimetics. Such compounds usually having a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonic acid) groups.

Two known classes of pseudopeptide or peptide mimetic MMP inhibitors have a hydroxamic acid group or a carboxylic group respectively as their zinc binding groups. With a few exceptions, such known MMPs may be represented by the structural formula (I)

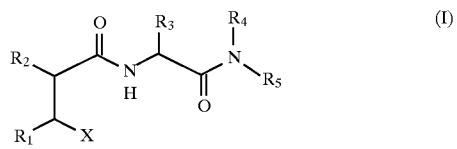

in which X is the zinc binding hydroxamic acid (—CONHOH) or carboxylic acid (—COOH) group and the groups $R_1$ to $R_5$ are variable in accordance with the specific prior art disclosures of such compounds. Examples of patent publications disclosing such structures are given below.

In such compounds, it is generally understood in the art that variation of the zinc binding group and the substituents $R_1$, $R_2$ and $R_3$ can have an appreciable effect on the relative inhibition of the metalloproteinase enzymes. The group X is thought to interact with metalloproteinase enzymes by binding to a zinc(II) ion in the active site. Generally the hydroxamic acid group is preferred over the carboxylic acid group in terms of inhibitory activity against the various metalloproteinase enzymes. However, the carboxylic acid group in combination with other substituents can provide selective inhibition of gelatinase (EP-489,577-A). The $R_1$, $R_2$ and $R_3$ groups are believed to occupy respectively the P1, P1' and P2' amino acid side chain binding sites for the natural enzyme substrate. There is evidence that a larger $R_1$ substituent can enhance activity against stromelysin, and that a $(C_1-C_6)$alkyl group (such as isobutyl) at $R_2$ may be preferred for activity against collagenase whilst an alkylphenyl group (such as phenylpropyl) at $R_2$ may provide selectivity for gelatinase over the other metalloproteinases.

Pseudopeptide or peptide mimetic MMP inhibitors of formula (I) with potent in vitro activities are known, but are generally poorly absorbed following oral administration. Although, it is known that a number of factors can influence oral absorption (such as aqueous solubility, pKa, log P and molecular weight) the design of pseudopeptide enzyme inhibitors with high oral absorption is far from straightforward. Finding a combination of $R_1$, $R_2$, $R_3$, $R_4$ or $R_5$ substituents that permits a good balance of intrinsic level of activity, water solubility, oral absobtion, and pharmacokinetic properties is a continuing problem in the art, since those properties can vary in an unpredictable way as the substituents $R_1-R_5$ are varied. Identifying hydroxamic and carboxylic acid-based MMP inhibitors having such properties remains a much sought after goal in the art.

Tumour necrosis factor (herein referred to as "TNF") is a cytokine which is produced initially as a cell-associated 28kD precursor. It is released as an active, 17kD form, which can mediate a large number of deleterious effects in vivo. When administered to animals or humans it causes inflammation, fever, cardiovascular effects, haemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal haematopoiesis in patients with these tumours.

Compounds which inhibit the production or action of TNF are therefore thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Recently, WO 93/120047 disclosed a class of hydroxamic acid based MMP inhibitors which also are active in inhibiting TNF production.

The following patent publications disclose hydroxamic acid- and carboxylic acid-based MMP inhibitors:

| US 4599361 | (Searle) |
| EP-A231081 | (ICI) |
| EP-A-0236572 | (Roche) |
| EP-A-0274453 | (Bellon) |
| WO 90/05716 | (British Biotech) |
| WO 90/05719 | (British Biotech) |
| WO 91/02716 | (British Biotech) |
| WO 92/09563 | (Glycomed) |
| US 5183900 | (Glycomed) |
| US 5270326 | (Glycomed) |
| WO 92/17460 | (SB) |
| EP-A-0489577 | (Celltech) |
| EP-A-0489579 | (Celltech) |
| EP-A-0497192 | (Roche) |
| US 5256657 | (Sterling) |
| WO 92/13831 | (British Biotech) |
| WO 92/22523 | (Research Corp) |
| WO 93/09090 | (Yamanouchi) |
| Wo 93/09097 | (Sankyo) |
| WO 93/20047 | (British Biotech) |
| WO 93/24449 | (Celltech) |
| WO 93/24475 | (Celltech) |
| EP-A-0574758 | (Roche) |
| EP-A-0575844 | (Roche) |
| WO 94/02446 | (British Biotech) |
| WO 94/02447 | (British Biotech) |
| WO 94/21612 | (Otsuka) |
| WO 94/21625 | (British Biotech) |
| WO 94/24140 | (British Biotech) |
| WO 94/25434 | (Celltech) |
| WO 94/25435 | (Celltech |

BRIEF DESCRIPTION OF THE INVENTION

Within the disclosures of the above patent publications compounds have been reported which have good in vitro activities as broad spectrum MMP inhibitors, and others which have good in vitro activities as inhibitors of one class of MMPs relative to the other classes, ie "selective" MMP inhibitory activity. However, there is a requirement for compounds which are not only potent MMP inhibitors in vitro, but also have good physico-chemical properties, such as water solubility, to facilitate formulation and administration, and which have desirable pharmacokinetic profiles after oral administration, for example producing high and/or prolonged effective concentrations in the blood.

This invention is based on the finding that compounds of formula (I) above wherein X a hydroxamic acid or carboxylic acid group, and $R_4$ is a group containing a plurality of ether linkages, have good intrinsic activity as MMP inhibitors, and good water solubility. The class of compounds of the invention also includes compounds which have pharmacokinetic properties, such as high and/or prolonged bioavailability after oral administration. In addition, the class includes compounds which inhibit the release of the pro-inflammatory cytokine TNF from cells.

Of the patent publications listed above, only EP-A-0489577, EP-A-0489579, WO 93/24449, WO 94/25434 and WO 94/25435 (Celltech) disclose compounds wherein the $R_4$ substituent includes "an optionally substituted straight or branched alkyl group, optionally interrupted by one or more —O—. . . atoms . . . ", a definition which encompasses substituents containing a plurality of ether linkages, but these disclosures are limited to compounds having a restricted range of substituents $R_2$ or $R_3$ not found in the compounds of the present invention. Furthermore, no specific examples are given of compounds having polyether $R_4$ substituents, no special attention is directed to the $R_4$ substituent, and there is no teaching of any advantage of such polyether $R_4$ substituents.

In addition, EP-A-0236872 discloses compounds wherein the substituent corresponding to $R_4$ in formula (I) above is 2,2-di($C_1$–$C_6$-alkoxy)ethyl, the specific disclosed example of such compounds being [4-(N-hydroxyamino)2(RS)-isobutylsuccinyl]-L-leucine-2,2-dimethoxyethylamide. However, there is no teaching in EP-A-0236872 of any advantage of the poyether substituents present in the compounds of the present invention.

DETAILED DESCRIPTION OF THE INVENTION

According to the present invention, there is provided a compound of general formula (I)

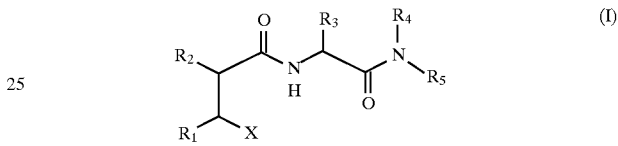

wherein

X is a —$CO_2H$ or —CONHOH group;

$R_1$ is hydrogen, a $C_1$–$C_6$ alkyl, $C_2$–$C_6$ alkenyl, phenyl, substituted phenyl, phenyl($C_1$–$C_6$ alkyl), heterocyclyl, substituted heterocyclyl, heterocyclyl($C_1$–$C_6$ alkyl), substituted heterocyclyl($C_1$–$C_6$ alkyl), or a group $BSO_nA$— wherein n is 0, 1 or 2 and B is hydrogen or a ($C_1$–$C_6$) alkyl, phenyl, substituted phenyl, heterocyclyl, $C_1$–$C_6$ acyl, phenacyl or substituted phenacyl group, and A represents $C_1$–$C_6$ alkyl; amino; protected amino; acylamino; OH; SH; $C_1$–$C_6$ alkoxy; $C_1$–$C_6$ alkylamino; $C_1$–$C_6$alkylthio; aryl($C_1$–$C_6$ alkyl); amino($C_1$–$C_6$ alkyl); hydroxy($C_1$–$C_6$ alkyl), mercapto ($C_1$–$C_6$ alkyl) or carboxy($C_1$–$C_6$ alkyl) wherein the amino-, hydroxy-, mercapto- or carboxyl-group are optionally protected or the carboxyl- group amidated; or lower alkyl substituted by maleimido, succinimido, naphthalimido, 2,3-dihydro-1,3-dioxo-1H-benz[d,e] isoquinol-2-yl, carbamoyl, mono(lower alkyl) carbamoyl, di(lower alkyl)carbamoyl, di(lower alkyl) amino, carboxy-lower alkanoylamino, pyrrolidino or morpholino;

$R_2$ is a $C_1$–$C_{12}$ alkyl, $C_2$–$C_{12}$ alkenyl, $C_2$–$C_{12}$ alkynyl, benzyl, cycloalkyl($C_1$–$C_6$alkyl)-, cycloalkenyl($C_1$–$C_6$ alkyl)-, phenyl($C_1$–$C_6$ alkyl)O($C_1$–$C_6$ alkyl)-, or heteroaryl($C_1$–$C_6$ alkyl)O($C_1$–$C_6$ alkyl)- group, any one of which may be optionally substituted by $C_1$–$C_6$ alkyl, $C_1$–$C_6$ alkoxy, halo or cyano (—CN);

$R_3$ is the side chain of a naturally occurring amino acid, which may be protected if functional groups are present, eg by acylation of amino groups and amidation of carboxyl groups; or a group —$CR_6R_7R_8$ in which each of $R_6$, $R_7$ and $R_8$ is independently hydrogen, ($C_1$–$C_6$)alkyl, ($C_2$–$C_6$)alkenyl, ($C_2$–$C_6$)alkynyl, phenyl ($C_1$–$C_6$) alkyl, halogen, —CN, —$CO_2H$, ($C_1$–$C_4$) perfluoroalkyl, —$CO_2(C_1$–$C_6)$alkyl, or a group phenyl or heteroaryl which is optionally substituted by one or more substituents independently selected from hydroxyl, halogen, —CN, —$CO_2H$, —$CO_2(C_1$–$C_6)$ alkyl, —CONH$_2$, —CONH(C$_1$-C$_6$)alkyl, —CONH(C$_1$—C$_6$alkyl)$_2$, —CHO, —CH$_2$OH, (C$_1$-C$_4$) perfluoroalkyl, —O(C$_1$-C$_6$)alkyl, —S(C$_1$-C$_6$)alkyl, —SO(C$_1$-C$_6$)alkyl, —SO$_2$(C$_1$-C$_6$)alkyl, —NO$_2$, —NH$_2$, —NH(C$_1$-C$_6$)alkyl, —N((C$_1$-C$_6$)alkyl)$_2$, —NHCO(C$_1$-C$_6$)alkyl, (C$_1$-C$_6$)alkyl, (C$_2$-C$_6$) alkenyl, (C$_2$-C$_6$)alkynyl, (C$_3$-C$_8$)cycloalkyl, (C$_4$-C$_8$) cycloalkenyl, phenyl or benzyl; or R$_6$ and R$_7$ together with the carbon atom to which they are attached form a 3 to 8 membered cycloalkyl or a 5- to 6-membered heterocyclic ring; or R$_6$, R$_7$ and R$_8$ together with the carbon atom to which they are attached form a bicyclic ring (for example adamantyl);

R$_4$ is a group of formula —(Z—O)$_n$—Z wherein Z is straight or branched C$_{1-6}$ alkyl optionally interrupted by one or more non-adjacent S and/or N atoms, n is an integer >1, and no continuous linear sequence of atoms in the group R$_4$ is >12, or a straight or branched C$_{2-6}$ alkyl group, optionally interrupted by one or more non-adjacent S and/or N atoms, which group is substituted by at least two substituents of formula —(Z)$_p$—(OZ)$_q$ wherein Z is straight or branched C$_{1-6}$alkyl optionally interrupted by one or more non-adjacent S and/or N atoms, p is 1, q is 1 or 2, and no continuous linear sequence of atoms in the group R$_4$ is >12;

R$_5$ is hydrogen or a (C$_1$-C$_6$)alkyl group;

or a salt, hydrate or solvate thereof.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, alpha-aminoadipic acid, alpha-amino-n-butyric acid, 3,4-dihydroxyphenylalanine, homoserine, alpha-methylserine, ornithine, pipecolic acid, and thyroxine. The amino acid side chains may be protected; for example the carboxyl groups of aspartic acid, glutamic acid and alpha-aminoadipic acid may be esterified (for example as a C$_1$-C$_6$ alkyl ester), the amino groups of lysine, ornithine, 5-hydroxylysine, 4-hydroxyproline may be converted to amides (for example as an, —NHCOC$_1$-C$_6$ alkyl amide) or carbamates (for example as an —NHC(=O)OC$_1$-C$_6$ alkyl or —NHC(=O)OCH$_2$Ph carbamate), the hydroxyl groups of 5-hydroxylysine, 4-hydroxyproline, serine, threonine, tyrosine, 3,4-dihydroxyphenylalanine, homoserine, alpha-methylserine and thyroxine may be converted to ethers (for example an —OC$_1$-C$_6$ alkyl or an —O(C$_1$-C$_6$ alkyl)phenyl ether) or esters (for example an —OC(=O)C$_1$-C$_6$ alkyl ester) and the thiol group of cysteine may be converted to thioethers (for example an —SC$_1$-C$_6$ alkyl thioether) or thioesters (for example an —SC(=O)C$_1$-C$_6$ alkyl thioester).

The term "cycloalkyl" as used herein means a saturated alicyclic ring having from 3–8 carbon atoms and includes, for example, cyclohexyl, cyclooctyl, cycloheptyl, cyclopentyl, cyclobutyl and cyclopropyl.

The term "cycloalkenyl" as used herein means an unsaturated alicyclic ring having from 5–8 carbon atoms and includes, for example, cyclohexenyl, cyclooctenyl, cycloheptenyl, and cyclopentenyl. The ring may contain more than one double bond.

As used herein the unqualified term "heterocyclyl" or "heterocyclic" refers to a 5–7 membered heterocyclic ring containing one or more heteroatoms selected from S, N and O, and optionally fused to a benzene ring, including for example, pyrrolyl, furyl, thienyl, imidazolyl, oxazolyl, thiazolyl, pyrazolyl, pyridinyl, pyrrolidinyl, pyrimidinyl, morpholinyl, piperizinyl, indolyl, benzimidazole, phthalimido, 1,2-dimethyl-3,5-dioxo 1,2,4-triazolidin-4-yl, 3-methyl-2,5-dioxo-1-imidazolidinyl and 3,44-trimethyl-2,5-dioxo-1 -imidazolidinyl.

As used herein, the term "heteroaryl" refers to a 5- or 6-membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be C$_1$-C$_6$ alkoxy, hydroxy, thio, C$_1$-C$_6$ alkylthio, amino, halo (including fluoro, chloro, bromo and iodo), cyano, trifluoromethyl, nitro, —COOH, —CONH$_2$, —CONHR$^A$ or —CONHR$^A$R$^A$ wherein R$^A$ is a C$_1$-C$_6$ alkyl group or the residue of a natural alpha-amino acid.

Salts of the compounds of the invention include physiologically acceptable acid addition salts for example hydrochlorides, hydrobromides, sulphates, methane sulphonates, p-toluenesulphonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as C atom carrying the R$_1$ and X groups-S, C atom carrying the R$_2$ group-R, C atom carrying the R$_3$ group-S, but mixtures in which the above configurations predominate are also contemplated.

In the compounds of the invention, a principal novelty characterising structural feature is the poyether group R$_4$. Subject to the definitions of the groups R$_1$, R$_2$, R$_3$, and R$_5$ set forth herein, each may be any of the groups which have been proposed in the corresponding positions of compounds disclosed in any of the patent publications listed above. Without limiting the generality of the foregoing:

Examples of particular R$_1$ groups include hydrogen, methyl, ethyl, n-propyl, hydroxyl, allyl, methoxy, and thienylmethylsulfanyl. Presently preferred are compounds in which R$_1$ is hydrogen, hydroxyl, n-propyl or allyl.

Examples of particular R$_2$ groups include iso-butyl, n-pentyl, n-hexyl, n-heptyl, n-nonyl, n-decyl, and benzyloxypropyl. Presently preferred are compounds in which R$_2$ is isobutyl.

Examples of particular R$_3$ groups include benzyl, iso-butyl, t-butyl, and 1-fluoro-1-methylethyl. Presently preferred are compounds in which R$_3$ is t-butyl.

R$_4$ may for example be a polyether chain possessing at least two non-adjacent oxygen atoms. Examples of particular R$_4$ groups include 2-(2-methoxyethoxymethoxy) ethyl, 1,1-dimethyl-2-(2-methoxyethoxymethoxy) ethyl, 2-(2-ethoxyethoxymethoxy)ethyl, 2-(2-(2-methoxyethoxy)ethoxy)ethyl, 2-(2-(3-methoxypropoxy)ethoxy)ethyl, 3-(2-methoxyethoxymethoxy) propyl, 2,2-dimethyl-3-(2-methoxyethoxymethoxy) propyl, 2-(2-ethoxyethoxy)ethyl, 2-(2-methoxyethoxy) ethyl, 3-(2-methoxyethoxy)propyl, 2,2-di(2-methoxymethyl) propyl, and 2,2-di(2-methoxymethyl)butyl. Presently preferred are compounds in which R$_4$ is 2-(2-methoxyethoxy)ethyl.

R$_5$ may for example be hydrogen, methyl or ethyl. Presently preferred are compounds in which R$_5$ is hydrogen.

A compound of the invention which is presently preferred for its good aqueous solubility and the high and prolonged effective blood concentrations produced after oral administration, is 2S-Allyl-N$^1$-hydroxy-3R-isobutyl-N$^4$-{1S-[2-(2-methoxy-ethoxy) -ethylcarbamoyl]-2,2-dimethyl-propyl}succinamide, and salts, solvates or hydrates thereof.

Other specific compounds of the invention are:

2S, N$^1$-Dihydroxy-3R-isobutyl-N$^4$-{1S-[2-(2-methoxy-ethoxymethoxy)ethylcarbamoyl]-2,2-dimethyl-propyl}-succinamide, 2S-Allyl-N$^1$-hydroxy-3R-isobutyl-N$^4$-{1S-[2-(2-methoxy-ethoxymethoxy) ethylcarbamoyl]-2-phenyl-ethyl}-succinamide, 2S-Allyl-N$^1$-hydroxy-3R-isobutyl-N$^4$-{1S-[2-(2-methoxy-ethoxymethoxy) ethylcarbamoyl]-2,2-dimethyl-propyl}-succinamide, 2S-Allyl-N$^1$-hydroxy-3R-isobutyl-N$^4$-(1S{2-[2-(2-methoxy-ethoxy)-ethoxy]-ethylcarbamoyl]-2,2-dimethyl-propyl}succinamide, 2S-Allyl-N$^4$-{1S-[2,2-di-(methoxymethyl)-propylcarbamoyl}2,2-dimethyl-propyl]-N$^1$-hydroxy-3R-isobutyl-succinamide, 2S-Allyl-N$^4$-{1S-[2,2-di-(methoxymethyl)-butylcarbamoyl]-2,2-dimethyl-propyl}N$^1$-hydroxy-3R-isobutyl-succinamide), N$^4$-Hydroxy-2R-isobutyl-N$^1$-{1S-[2-(2-methoxy-ethoxy) -ethylcarbamoyl]-2,2-dimethyl -propyl}-3S-(thiophen-2-yl-sulfanylmethyl)-succinamide), N$^4$-Hydroxy-2R-isobutyl-N$^1$-(1S-{2-[2-(2-methoxy-ethoxy)-ethoxy]-ethylcarbamoyl)}-2,2-dimethyl-propyl)-3S-(thiophen-2-yl-sulfanylmethyl)-succinamide), N$^1$-{1S-[2,2-Di-(methoxymethyl)-propylcarbamoyl]-2,2-dimethyl-propyl}-N$^4$-hydroxy -3R-isobutyl-3S-(thiophen-2-yl-sulfanylmethyl)-succinamide, N$^4$-Hydroxy-2R-isobutyl-N$_1$-{1S-[2-(2-methoxy-ethoxy) -ethylcarbamoyl]-2,2-dimethyl -propyl}-3S-propyl-succinamide), and salts, solvates or hydrates thereof.

Compounds according to the present invention in which X is a hydroxamic acid group —CONHOH may be prepared from compounds of the invention in which X is a carboxylic acid group —COOH. That process, which forms another aspect of the invention, comprises reacting an acid of general formula (II)

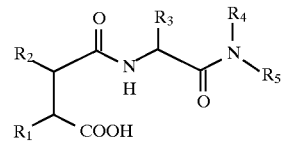

or an activated derivative thereof with hydroxylamine, O-protected hydroxylamine, or an N,O-diprotected hydroxylamine, or a salt thereof, R$_1$, R$_2$, R$_3$, R$_4$, and R$_5$ being as defined in general formula (I) except that any substituents in R$_1$, R$_2$, R$_3$, R$_4$, and R$_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in R$_1$, R$_2$, R$_3$, R$_4$, and R$_5$.

Conversion of (II) to an activated intermediate such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, tert-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

In the special case where R$_1$ in compound (I) is hydroxy, it too may be protected during the coupling of compounds (II) with hydroxamic acid. In that case a particularly useful technique may be simultaneous protection of the hydroxy group R$_1$ and the adjacent carboxyl group as a dioxalone of formula (IIa):

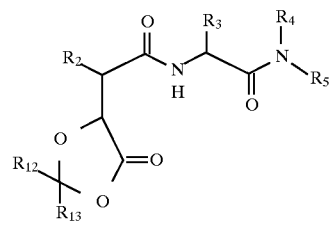

wherein the groups R$_{12}$ and R$_{13}$ are derived from a dioxalone forming reagent, and may be, for example, hydrogen, alkyl, phenyl or substituted phenyl. The dioxalone ring is opened on reaction with hydroxylamine to give the required hydroxamic acid derivative of formula (I).

Compounds according to the present invention in which X is a carboxylic acid group —COOH may be prepared by a process comprising: coupling an acid of formula (IV) or an activated derivative thereof with an amine of formula (V)

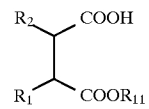

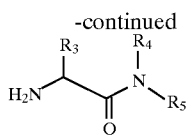

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$, and $R_5$.

Active derivatives of acids (IV) include activated esters such as the pentafluorophenyl ester, acid anhydrides and acid halides, eg chlorides. Suitable hydroxy protecting groups may be selected from those known in the art.

In the special case where $R_1$ in compound (IV) is hydroxy, it too may be protected during the coupling of compounds (IV) and (V). In that case a particularly useful technique may be simultaneous protection of the two hydroxy groups as a dioxalone of formula (VI):

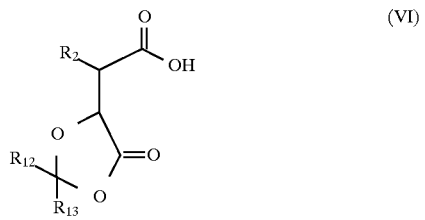

wherein the groups $R_{12}$ and $R_{13}$ are derived from a dioxalone forming reagent, and may be, for example, hydrogen, alkyl, phenyl or substituted phenyl.

Starting materials (V) may be prepared from the corresponding alpha amino acids $H_2N$—$CH(R_3)$—COOH either by amide formation with the corresponding polyether amine $HNR_4R_5$, or by succesive formation of the desired ether linkages starting from the the appropriate hydroxyalkylamide of the alpha amino acid.

Starting materials (IV), and and the alpha amino acid starting materials referred to in the preceding paragraph are either known or are prepared by routine known synthetic methods, for example as in the relevant patent publications listed above.

As mentioned above, compounds of formula (I) are useful in human or veterinary medicine since they are active as inhibitors of MMPs, and a further advantage lies in their ability to inhibit the release of tumour necrosis factor (TNF) from cells.

Accordingly in another aspect, this invention concerns:
(i) a method of management (by which is meant treatment or prophylaxis) of diseases or conditions mediated by MMPs and/or TNF in mammals, in particular in humans, which method comprises administering to the mammal an effective amount of a compound as defined with respect to formula (I) above, or a pharmaceutically acceptable salt thereof; and
(I) a compound as defined with respect to formula (I) for use in human or veterinary medicine, particularly in the management (by which is meant treatment or prophylaxis) of diseases or conditions mediated by MMPs and/or TNF; and
(iii) the use of a compound as defined with respect to formula (I) in the preparation of an agent for the management (by which is meant treatment or prophylaxis) of diseases or conditions mediated by MMPs and/or TNF.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. In view of the water-solubility, and oral bioavailability advantanges of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, for example from about 10 to 250 mg of a compound of the invention. A suitable daily dose for a mammal may vary widely depending on the condition of the patient. However, a dose of a compound of general formula I of about 0.1 to 300 mg/kg body weight, particularly from about 1 to 100 mg/kg body weight may be appropriate.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The dosage for topical administration will of course depend on the size of the area being treated. For the eyes, each dose may typically be in the range from 10 to 100 mg of the drug.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

The following Examples illustrate embodiments of the invention:

The amino acids used in the examples were commercially available or were prepared according to literature procedures.

The following abbreviations have been used throughout:

| | |
|---|---|
| DIPE | Diisopropyl ether |
| DMF | N,N-Dimethylformamide |
| EDC | N-Ethyl-N'-(3-dimethylaminopropyl)carbodiimide hydrochloride |
| HOBt | 1-Hydroxybenzotnazole |
| LDA | Lithium N,N-diisopropylamide |
| NMM | N-Methylmorpholine |
| THF | Tetrahydrofuran |
| TFA | Trifluoroacetic acid |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by CHN Analysis Ltd., Alpha House, Countesthorpe Road, South Wigston, Leicester, LE8 2PJ, UK and MEDAC Ltd., Department of Chemistry, Brunel University, Uxbridge, Middlesex UB8 3PH.

EXAMPLE 1

2S, N$^1$-Dihydroxy-3R-isobutyl-N$^4$-{1S-[2-(2-methoxy-ethoxymethoxy)-ethylcarbamoyl]-2,2-dimethyl-propyl}-succinamide

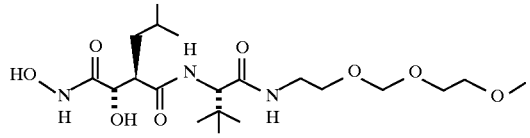

STEP A:

2S-Hydroxy-3R-(2-methyl-allyl)-succinic acid diisopropyl ester

2S-Hydroxy-succinic diisopropyl ester (50 g, 230 mmol) was added to a solution of LDA [from N,N-diisopropylamine (80 ml, 570 mmol) and 10M n-butyllithium (48.1 ml, 481 mmol)] in dry THF (500 ml) whilst maintaining the temperature at −70° C. When addition was complete the reaction was warmed to −15° C. and stirred for 8 hours.

The reaction mixture was cooled to −70° C. and methallyl iodide (46 g, 252 mmol) was added slowly, ensuring that the temperature did not exceed −65° C. The mixture was warmed to 40° C. and stirred for 18 hours before quenching at −15° C. with citric acid. The organic layer was separated and washed with 10% aq. sodium hydrogen carbonate solution (500 ml) and brine (300 ml) then dried over magnesium sulphate. The solution was filtered and concentrated in vacuo to give a brown oil (64 g) which was purified by column chromatography (silica gel, 1 kg, gradient elution with 20 to 35% diethyl ether in hexane). The desired product was isolated as a colourless oil (30.9 g, 49%) which was found to be a 17:1 mixture of diastereomers by NMR. $^1$H —NMR; δ(CDCI$_3$, major diastereomer), 5.06 (1H, septet, J=6.3 Hz), 4.97 (1H, septet, J=6.3 Hz), 4.78 (2H, d, J=7.1 Hz), 4.16 (1H, m), 3.20 (1H, d, J=6.2 Hz), 3.00 (1H, m), 2.50, 2.35 (2H, ABX, J=7.0, 8.7, 14.4 Hz), 1.72 (3H, s) and 1.24–1.16 (12H, 2 m).

STEP B:

2S-Hydroxy-3R-isobutyl-succinic acid diisopropyl ester

2S-Hydroxy-3R-(2-methyl-allyl)-succinic acid diisopropyl ester (7.14 g, 26.2 mmol) was dissolved in ethanol (80 ml), and stirred overnight with 10% palladium on charcoal catalyst (1.0 g) under an atmosphere of hydrogen. The catalyst was removed by filtration and the filtrate was evaporated to dryness to leave the product as a clear oil (7.03 g, 98%). $^1$H—NMR; δ(CDCI$_3$), 5.06 (1H, septet, J=6.3 Hz), 4.97 (1H, septet, J=6.3 Hz), 4.17 (1H, br s,), 3.24 (1H, br s), 2.83 (1H, m), 1.68 (2H, m), 1.44 (1H, m), 1.24 (6H, d, J=6.2 Hz), 1.18 (6H, d, J=6.2 Hz) and 0.89 (6H, m).

STEP C:

2S-Hydroxy-3R-isobutyl-succinic acid

2S-Hydroxy-3R-isobutyl-succinic acid diisopropyl ester (7.0 g, 25.6 mmol) was dissolved in dioxane (15 ml) and water (15 ml), a solution of potassium hydroxide (4.29 g) in water (22 ml) was added and the mixture was heated at 90° C. overnight. The solution was allowed to cool and then passed through an ion exchange resin (Dowex 50×4-400, 200 ml) and evaporated to yield the title compound (4.82 g, 99%). $^1$H—NMR; δ(CDCI$_3$), 8.70 (2H, br s), 4.32 (1H, br s), 3.10 (1H, m), 1.85–1.55 (3H, m) and 0.96 (6H, m).

STEP D:

2R-(2,2-Dimethyl-5-oxo-[1,3]dioxalan4S-yl)4-methylpentanoic acid

2S-Hydroxy-3R-isobutyl-succinic acid (5.19 g, 27.3 mmol) was dissolved in 2,2-dimethoxypropane (150 ml) and DMF (40 ml) and stirred overnight at 30° C. in the presence of a catalytic amount of p-toluene sulphonic acid. The solvent was removed to give the title compound contaminated with solvent (6.87 g, crude). $^1$H —NMR; δ(CDCI$_3$), 4.41 (1H, d, J=4.8 Hz), 2.91 (1H, m), 1.69 (3H, m), 1.54 (3H, s), 1.48 (3H, s) and 0.88 (6H, m).

STEP E:

2R-(2,2-Dimethyl-5-oxo-[1,3]dioxalan-4S-yl)4-methylpentanoic acid pentafluorophenyl ester 2R-(2,2-Dimethyl-5-oxo-[1,3]dioxalan4S-yl)4-methylpentanoic acid (558 mg, 2.4 mmol) was taken up in dichloromethane (10 ml) and cooled to 0° C. before adding pentafluorophenol (670 mg, 3.6 mmol) and EDC (560 mg, 2.9 mmol). The reaction was stirred at 0° C. for 2 hours then the solution was washed with 1M sodium carbonate (50 ml) and brine (20 ml). The organic layer was dried (magnesium sulphate), filtered, evaporated to dryness and purified by column chromatography (silica gel, dichloromethane) to give the activated ester (552 mg, 58%). $^1$H—NMR;

δ(CDCl₃), 4.57 (1H, d, J=6.5 Hz), 3.32 (1H, m), 1.86 (3H, m), 1.67 (3H, s), 1.58 (3H, s) and 1.03 (6H, m).

STEP F:

N-Benzyloxycarbonyl-O-(2-methoxyethoxymethyl) ethanolamine

To a cooled (0° C.) solution of N-benzyloxycarbonyl-ethanolamine (12.03 g, 61.6 mmol) in dry dichloromethane (50 ml) was added diisopropylethylamine (32.2 ml, 184.9 mmol) and 2-methoxyethoxymethyl chloride (16.9 ml, 147.9 mmol) with stirring. The mixture was allowed to warm to room temperature then stirred for a further 3 hours. The solvent was removed under reduced pressure and the residue was taken up in ethyl acetate and washed successively with 1M hydrochloric acid, sat. aq. sodium hydrogen carbonate and brine. The organic phase was dried over magnesium sulphate, filtered and evaporated to porvide the title compound as a orange/yellow oil which was used without further purification. ¹H—NMR; δ(CDCl₃), 7.35 (5H, m), 5.45 (1H, m), 5.11 (2H, s), 4.72 (2H, s), 3.67 (4H, m), 3.55 (2H, m) and 3.38 (5H, m).

STEP G:

O-(2-methoxyethoxymethyl)ethanolamine

N-Benzyloxycarbonyl-O-(2-methoxyethoxymethyl) ethanolamine (6.25 g, 22.0 mmol) was dissolved in ethanol (10 ml) and placed under a blanket of argon. A slurry of 10% palladium on charcoal (1 g) in ethyl acetate was added and hydrogen gas was bubbled through the suspension for 3 hours and then the mixture was placed under hydrogen atmosphere overnight. TLC indicated that some starting material still remained so a further batch of catalyst (1 g) was added and hydrogenation was allowed to continue for a further 6 hours, after which all the starting material had been consumed. The catalyst was removed by filtration and the filtrate was used directly in Example 1 *h* (product volatile).

STEP H:

N-Benzyloxycarbonyl-L-tert-leucine-N-2-(2-methoxy-ethoxymethoxy)ethylamide

N-Benzyloxycarbonyl-L-tert-leucine (2.01 g, 7.6 mmol) was dissolved in DMF (20 ml), cooled in an ice bath and stirred during the addition of pentafluorophenol (2.83 g, 15.4 mmol) and EDC (2.95 9, 15.4 mmol). The mixture was stirred at 0° C. for 1 hour then at room temperature for a further 2 hours. The solution was cooled back to 0° C., a solution of O-(2-methoxyethoxymethyl) ethanolamine in ethanol, prepared in StepG, was added and the reaction was allowed to stir overnight at room temperature. The solvent was removed under reduced pressure, the residue was dissolved in diethyl ether (50 ml), and the solution was washed successively with 1M sodium carbonate (2×30 ml), 1M hydrochloric acid (2×30 ml) and brine (30 ml). The organic phase was dried over magnesium sulphate, filtered and evaporated to an oil which was purified by column chromatography (silica gel, gradient elution with 50–75% ethyl acetate in hexane). Yield: 1.79 g (67%). ¹H—NMR; δ(CDCl₃), 7.34 (5H, m), 6.54 (1H, m), 5.60 (1H, m), 5.11 (2H, m), 4.62 (2H, s), 3.93 (1H, d, J=9.3 Hz), 3.70 (4H, m), 3.57 (3H, m), 3.44 (3H, s), 3.41 (1H, m) and 1.00 (9H, s).

STEP I:

L-tert-Leucine-N-2-(2-methoxy-ethoxymethoxy) ethylamide

N-Benzyloxycarbonyl-L-tert-leucine-N-2-(2-methoxy-ethoxymethoxy)ethylamide was deprotected by hydrogenolysis, as described in Step G. Reaction was complete after 3 hours, leaving a single ninhydrin positive spot on TLC (5% methanol in dichloromethane). The solvent wwas removed to give the title compound as a white foam. Yield: 1.17 9(92%). ¹H—NMR; δCD₃OD), 4.66 (2H, s), 3.68–3.48 (7H, br m), 3.40 (1H, m), 3.35 (3H, s) and 0.95 (9H, s).

STEP J:

2R-(2,2-Dimethyl-5-oxo-[1,3]dioxalan-4S-yl)4-methylpentanoic acid {1-[2-(2-methoxy-ethoxymethoxy)-ethylcarbamoyl]-2,2-dimethyl-propyl}-amide The product from Step E (1.79 g, 6.0 mmol) was dissolved in DMF (4 ml) and cooled to 0° C. during the addition of a solution of L-tert-leucine-N-2-(2-methoxy-ethoxymethoxy)ethylamide (1.50 g, 5.71 mmol) in DMF (3 ml). The solution was stirred for 10 minutes at 0° C., then overnight at 30° C. TLC (5% methanol in dichloromethane) indicated that little starting material remained. The solvent was removed under reduced pressure and the residue was dissolved in diethyl ether, and washed successively with water, 1M sodium carbonate and brine. The organic phase was dried over magnesium sulphate, filtered and evaporated under reduced pressure to leave a waxy solid which was recrystallised from ethyl acetate-hexane. Yield (1.32 g, 46%). ¹H—NMR; δ(CDCl₃), 6.59 (1H, d, J=9.3 Hz), 6.52 (1H, m), 4.69 (2H, s), 4.47 (1H, d, J=6.1 Hz), 4.22 (1H, d, J 9.3 Hz), 3.71 (2H, m), 3.65 (2H, m), 3.56 (2H, m), 3.55–3.30 (2H, br m), 3.43 (3H, s), 2.72 (1H, m), 1.75 (1H, m), 1.63 (1H, m), 1.62 (3H, s), 1.53 (3H, s), 1.00 (9H, s), 0.91 (3H, d, J =6.2 Hz) 0.91 (1H, m) and 0.90 (3H, d, J=6.3 Hz).

STEP K:

2S, N¹-Dihydroxy-3R-isobutyl-N⁴-{1S-[2-(2-methoxy-ethoxymethoxy)ethylcarbamoyl]-2,2-dimethyl-propyl}-succinamide Hydroxylamine hydrochloride (0.71 g, 10.2 mmol) was dissolved in methanol (10 ml), anhydrous sodium methoxide (0.55 g, 10.2 mmol) was added and the mixture was stirred for 2 hours at room temperature. The residual solid was removed by fltration and the filtrate was cooled to 0° C. during portionwise addition of 2R-(2,2-dimethyl-5-oxo-[1,3]dioxalan4S-yl)4-methylpentanoic acid {1-[2-(2-methoxy-ethoxymethoxy) -ethylcarbamoyl]-2,2-dimethyl-propyl}-amide. The solution was stirred for 10 minutes at 0° C. then overnight at room temperature. The solvent was removed under reduced pressure and the residue was purified by column chromatography (acid-washed silica, gradient elution with 2–10% methanol in dichloromethane) followed by recrystallisition from methanol-DIPE. Yield: 0.81 g (70%). ¹H—NMR; δ(CD₃OD) 4.65 (2H, s), 4.22 (1H, s), 4.00 (1H, d), 3.68–3.25 (8H, br m), 3.33 (3H, s), 2.81 (1H, m), 1.60 (1H, m), 1.50 (1H, m), 1.25 (1H, m), 0.96 (9H, s), 0.89 (3H, d, J=6.4 Hz) and 0.85 (3H, d, J=6.5 Hz). ¹³C—NMR; δ(CD₃OD), 175.72.7, 171.5, 96.6, 73.0, 73.0, 68.0, 67.5, 62.0, 59.1, 40.4, 39.7, 35.4, 27.2, 26.9, 23.6 and 22.4. Found: C, 53.34, H, 8.67, N, 9.20%; C₂₀H₃₉N₃O₈ requires: C, 53.44, H, 8.74, N, 9.35%.

EXAMPLE 2

2S-Allyl-N¹-hydroxy-3R-isobutyl-N⁴-{1S-[2-(2-methoxy-ethoxymethoxy) ethylcarbamoyl]-2-phenyl-ethyl}-succinamide

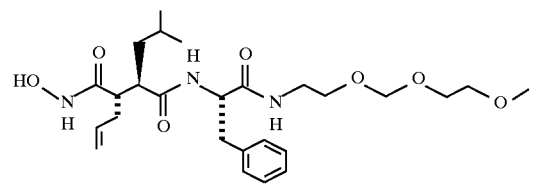

STEP A:

4S-Benzyl-3-(4-methyl-pentanoyl)-oxazolidin-2-one

A dry 500 ml flask equipped with a magnetic stirrer was charged with 4S-benzyl -oxazolidin-2-one (17.72 g, 100 mmol), this was capped with a rubber septum and flushed with nitrogen. Anhydrous THF (300 ml) was added via a cannula and the resulting solution was cooled to −78° C. in an acetone/dry-ice bath. A solution of 1.47M n-butyllithium in hexane (68.4 ml, 101 mmol) was transferred via cannula to a dry, septum-stoppered 100 ml dropping funnel. This was added dropwise to the THF solution over 10 minutes. 4-Methylvaleric acid chloride (14.80 g, 110 mmol) was added in one portion by syringe after completion of the addition of n-butyllithium. The resulting solution was stirred at −78° C. for 30 minutes and then allowed to warm to ambient temperature over 30 minutes. Excess acid chloride was quenched by the addition of aq. ammonium chloride (60 ml) and the bulk of the solvent was removed under reduced pressure. The resulting slurry was extracted with dichloromethane (2 ×80 ml). The combined organic extracts were washed with 1M sodium hydroxide (75 ml), brine (75 ml), dried over anhydrous sodium sulphate and filtered. The solvent was removed to yield the title compound as a yellow oil (29.20 g, crude). $^1$H —NMR; δ(CDCI$_3$), 7.34–7.19 (5H, m), 4.73–4.63 (1H, m), 4.25–4.16 (2H, m), 3.30 (1H, dd, J=3.3 Hz), 3.05–2.85 (2H, m), 2.78 (1H, dd, J=9.5 Hz), 1.76–1.53 (3H, m) and 0.97 (6H, d, J=6.2 Hz).

STEP B:

3-(4S-benzyl-2-oxo-oxazolidine-3-carbonyl)-5-methyl-hexanoic acid-4-tert-butyl ester)

4S-Benzyl-3-(4-methyl-pentanoyl)-oxazolidin-2-one (20 g, 72.6 mmol) was placed in a dry 1 liter 3-necked flask to which was added dry THF (400 ml). The mixture was kept under a stream of argon and cooled to −78° C. (dry ice/acetone). Sodium bis(trimethyl)silylamide (1M solution in THF, 72.6 ml, 72.6 mmol) was added dropwise through a dropping funnel. After stirring for 20 minutes, tert-butyl bromoacetate (21.02 g, 15.8 ml, 109 mmol) was added dropwise over 1 minute, to give an orange solution. The mixture was kept at −78° C. and allowed to warm to −50° C. over 2 hours (after which time it turned pink). The reaction was then quenched by adding acetic acid (10.90 g, 10.4 ml, 182 mmol) in ether (50 ml) at −50° C., whereupon the solution became colourless. The solvent was removed under reduced pressure and the resulting slurry was partitioned between ethyl acetate and brine. The ethyl acetate layer was washed once with brine and the original brine layer was back-extracted with ethyl acetate. The combined organic layers were dried and the solvent removed, giving a yellow oil which crystallised on cooling overnight to yield the title compound as a crystalline solid (21.36 g, 76%). $^1$H—NMR; δ(CDCI$_3$), 7.38–7.24 (5H, m), 4.724.62 (1H, m), 4.354.20 (1H, m), 4.18–4.16 (2H, m), 3.36 (1H, dd, J=3.25 Hz), 2.72 (1H, dd, J=2.3 Hz), 2.49 (1H, dd, J=4.6 Hz), 1.72–1.24 (3H, m), 1.44 (9H, s) and 0.96–0.91 (6H, dd, J=4.5 Hz). [α]$^{25}_D$=+66.90°(c=1, MeOH).

STEP C:

2R-isobutyl-succinic acid-4-tert-butyl ester 3-(4S-benzyl-2-oxo-oxazolidine-3-carbonyl)-5-methyl-hexanoic acid-4-tert-butyl ester) (15.30 g, 39 mmol) was placed in a 1 liter flask with a stirrer bar and to it was added a mixture of THF (600 ml) and water (150 ml). The solution was stirred and cooled to 0° C. (ice/acetone bath) then 60% aq. H$_2$O$_2$ (4.5 ml, 157 mmol) was added via syringe over 5 minutes, followed by lithium hydroxide (2.65 g, 63 mmol) in 100 ml water. The reaction mixture was stirred for 1 h at 0° C. TLC (10% methanol in dichloromethane) showed complete reaction (product gave a yellow spot on TLC on staining with bromocresol green and heating). The reaction mixture was quenched with sodium nitrite (10.88 g, 157 mmol), the final pH was 12–13. THF was removed in-vacuo and the aqueous layer was extracted with dichloromethane (3×200 ml) to recover the chiral auxiliary. The organic extracts were dried over anhydrous magnesium sulphate, filtered and the solvent removed in-vacuo and the resulting solid chiral auxiliary (7.05 g, 39 mmol, 100%) recrystallised from ethyl acetate-hexane (2:1) [α]$^{25}_D$=13.0°(c=1, methanol). The aqueous layer was cooled in an ice bath and acidified to pH 5–6 with 2M hydrochloric acid. The resulting cloudy solution was extracted with ethyl acetate (4×200 ml), readjusting the pH to 5–6 in between extractions. The combined organic extracts were dried over magnesium sulphate, filtered and the solvent was removed to yield the title compound as a pale yellow oil (8.21 g, 91%). $^1$H—NMR; δ(CDCI$_3$), 2.85 (1H, m), 2.59 (1H, dd, J=16, 9 Hz), 2.38 (1H, dd, J=16, 5 Hz), 1.64 (1H, m), 1.28 (1H, m) and 0.93 (6H, dd, J=7, 8 Hz). [α]$^{25}_D$=+10.4°(c=1, MeOH)

STEP D:

2R,S-Allyl-3R-isobutyl-succinic acid-4-tert-butyl ester (1:9, RS:RR)

To a stirred solution of 2R-isobutyl-succinic acid-4-tert-butyl ester (5 g, 21.7 mmol) in dry THF (100 ml), under an argon atmosphere, at −78° C., was added 1.5M LDA (31.8 ml, 47.74 mmol) dropwise via cannula. After stirring the solution at −78° C. for 1 hour, allyl bromide (2.44 ml, 28.21 mmol) was added dropwise via syringe. The resulting solution was allowed to warm to room temperature over a 2 hour period. Methanol (10 ml) was added and the solution stirred at room temperature. After 30 minutes the reaction mixture was concentrated under reduced pressure. The residue was taken up in dichloromethane (100 ml) and washed with 1M hydrochloric acid (100 ml) and brine (100 ml). The dichloromethane layer was dried over magnesium sulphate filtered and solvent removed under reduced pressure to give the title compound as a golden oil (5.6 g, 96.7%) (1:9, RS:RR) $^1$H—NMR; δ(CDCI$_3$, major diastereoisomer), 5.78–5.63 (1H, m), 5.01–5.11 (2H, m), 2.72–2.57 (2H, m), 2.37 (2H, m), 1.67–1.52 (2H, m), 1.42 (9H, s), 1.37 (1H, m) and 0.90 (6H, d, J=6.3 Hz). $^{13}$C—NMR; δ(CDCI$_3$ major diastereoisomer) 181.1, 172.9, 134.6, 117.3, 81.2, 47.8, 44.3, 38.4, 27.9, 25.9, 23.5, and 21.5.

STEP E:

3R,S-Allyl-2R-isobutyl-succinic acid-4-tert-butyl ester (3:1, RS:RR)

(i) To a stirred solution of 2R,S-allyl-3R-isobutyl-succinic acid-4-tert-butyl ester (1:9, RS:RR) (1:9, RS:RR) (5.11 g, 18.9 mmol) in dry THF (100 ml) under argon at −78° C. was added 1.5M LDA (27.7 ml, 41.6 mmol) via cannula. The reaction mixture was warmed to room temperature over a 2 hour period then cooled back to −780° C. and methanol (8 ml) was added via syringe. The reaction was then allowed to warm to room temperature for a further 2 hours. The solvent was removed under reduced pressure. The residue was taken up in dichloromethane (150 ml) and washed with 1M hydrochloric acid (150 ml) and brine (150 ml). The dichloromethane layer was dried over magnesium sulphate and the solvent removed under reduced pressure to yield the title compound (3:2, RS:RR), as a brown oil (4.7 g, 92%).

(ii) Utilising the epimerisation procedure described in Example 2e(i), but employing a reaction temperature of −78° C. after addition of LDA in lieu of allowing, the reaction mixture to warm to room temperature yielded the title compound, as the major diastereomer as a brown oil (4.6 g, 98%) (3:1, RS:SR). $^1$H—NMR; δ(CDCI$_3$, major diastereoisomer), 11.60 (1H, br s), 5.75–5.61 (1H, br m), 5.06–4.96 (2H, br m), 2.70–2.52

(2H, br m), 2.36–2.19 (2H, br m), 1.65–1.44 (2H, br m), 1.40 (9H, s), 1.13 (1H, m) and 0.86 (6H, dd, J=4.4, 2.1 Hz). $^{13}$C—NMR; δ(CDCl$_3$, major diastereoisomer) 180.7, 172.2, 134.6, 117.1, 81.0, 48.6, 45.7, 38.9, 34.8, 33.4, 27.9, 26.2 and 21.2.

STEP F:

3R,S-Allyl-2R-isobutyl-succinic acid 1-pentafluorophenyl ester 4 tert-butyl ester (3:1, RS:RR)

To a stirred solution of 3R,S-Allyl-2R-isobutyl-succinic acid-4 tert-butyl ester (4.60 g, 17.2 mmol) (3:1, RS:RR) in dichloromethane (50 ml) was added pentafluorophenol (6.13g, 33.3 mmol). The reaction mixture was cooled to 0° C. and NMM (2.02 g, 20.0 mmol) and EDC (3.94 g, 20.0 mmol) were added. The reaction mixture was allowed to warm to room temperature and stirred for 12 hours. The solvent was removed under reduced pressure. The residue was taken up in dichloromethane (50 ml) and washed with 1M hydrochloric acid (3×50 ml), saturated sodium bicarbonate (3×50 ml) and brine (50 ml). The dichloromethane layer was dried over magnesium sulphate filtered and the solvent removed under reduced pressure to give a brown oil. Column chromatography (flash silica, dichloromethane) yielded the title compound as a golden oil (5.47 g, 74%) (3:1, RS:SR). $^1$H—NMR; δ(CDCl$_3$, major diastereoisomer), 5.85–5.67 (1H, bm), 5.17–5.05 (2H, bm), 3.10–3.01 (1H, m), 2.79–2.69 (1H, m), 2.51–2.29 (2H, br m), 1.88–1.61 (2H, br m), 1.46 (9H, s), 1.37–1.24 (1H, m) and 0.96 (6H, dd, J=4.0, 4.5 Hz). $^{13}$C—NMR; δ(CDCl$_3$, major diastereoisomer), 171.5, 170.3, 134.1, 117.5, 81.4, 48.8, 45.8, 39.5, 35.0, 27.9, 26.3, 23.5, and 21.0.

STEP G:

N-Benzyloxycarbonyl-L-phenylalanine-N-(2-hydroxylethyl)amide.

To a stirred solution of N$^a$-benzyloxycarbonyl-L-phenylalanine (10 g, 33.0 mmol) at 0° C. was added pentafluorophenol (9.2 g, 50.0 mmol) followed by EDC (7.6 g, 39.0 mmol). The reaction mixture was allowed to warm to room temperature, stirred for 2 hours and then ethanolamine (1.8 ml, 43.0 mmol) was added and stirring was continued overnight. The solvent was removed under reduced pressure to leave a yellow oil which was purified by column chromatography (silica gel, 0–5% methanol in dichloromethane) followed by trituration with ethyl acetate-hexane. Yield: 16.2 g (contained residual hexane). $^1$H—NMR; δ(CDCl$_3$), 7.34–7.18 (10H, m), 6.39 (1H, br s), 5.59 (1H, d, J=7.6 Hz), 5.05 (2H, m), 4.39 (1H, m), 3.53 (2H, br s), 3.29 (2H, m), 3.06 (2H, m).

STEP H:

N-Benzyloxycarbonyl-L-phenylalanine-N-2-(2-methoxy-ethoxymethoxy)ethylamide

To a solution of N-benzyloxycarbonyl-L-phenylalanine-N-(2-hydroxylethyl)amide (7.0 g, 20.4 mmol) in dry dichloromethane (150 ml) under an argon atmosphere was added 2-methoxyethoxymethyl chloride (5.6 ml, 49.0 mmol) and diisopropylethylamine (10.7 ml, 61.4 mmol). The reaction mixture was stirred overnight at room temperature, after which time starting material was still detectable by TLC. The solvent volume was concentrated to one third, an equal volume of DMF was added and the reaction mixture was stirred for a further 60 hours at room temperature. The solvents were removed under reduced pressure, the residue was dissolved in ethyl acetate and washed successively with 1M hydrochloric acid, sat. aq. sodium hydrogen carbonate and brine. The organic phase was dried over sodium sulphate, filtered and concentrated to afford the desired product as a pale yellow oil which crystallised when left under high vacuum for ca. 1 hour. Yield: 8.0 g (90%). $^1$H—NMR; δ(CDCl$_3$), 7.33–7.14 (10H, m), 6.84 (1H, br s), 5.89 (1H, br s), 5.01 (2H, m), 4.54 (2H, s), 4.46 (1H, m), 3.56–3.26 (11H, m), 3.02 (2H, m).

STEP I:

L-Phenylalanine-N-2-(2-methoxy-ethoxymethoxy) ethylamide

The product from Example 2h(8.0 g, 18.3 mmol) was dissolved in ethanol (200 ml) and placed under a blanket of argon. 10% palladium on charcoal (800 mg) was added as a slurry in ethyl acetate and the mixture was then stirred under an atmosphere of hydrogen. After 4 hours no starting material could be detected on TLC. The catalyst was removed by filtration and the filtrate was concentated under reduced pressure to provide the title compound as a foam. Yield: 5.36 g (ca. quant.). $^1$H—NMR; δ(CDCl$_3$), 7.54 (1H, br s), 7.30–7.16 (5H, m), 4.65 (2H, s), 3.65–3.33 (12H, m), 3.20, 2.65 (2H, ABX, J=13.7, 9.2, 4.2 Hz) and 1.73 (2H, br s).

STEP J:

2S-(1R-{1S-[2-(2-Methoxy-ethoxymethoxy)-ethylcarbamoyl]-2-phenyl-ethylcarbamoyl}-3-methyl-butyl)-pent-4-enoic acid tert-butyl ester The products from Example 2i(5.36 g, 21.4 mmol) and Example 2f(7.79 g, 17.8 mmol) were dissolved together in DMF (50 ml) and stirred at room temperture overnight. TLC revealed that all of the pentafluorophenyl ester had been consumed.

The solvent was removed under reduced pressure and the residue was dissolved in ethyl acetate and washed successively with 1M hydrochloric acid, 1M sodium carbonate and brine. The organic phase was dried over sodium sulphate, filtered and concentrated to a yellow oil which was purified by column chromatography (silica gel, 2–10% methanol in dichloromethane). Crystallisation from ethyl acetate -hexane afforded the desired product as a white solid. Yield: 2.5 g (26%, single diastereoisomer). $^1$H—NMR; δ(CDCl$_3$), 7.27–7.21 (5H, m), 6.43 (2H, m), 5.60 (1H, m), 4.97 (2H, m), 4.60 (3H, m), 3.62–3.38 (11H, m), 3.06 (2H, m), 2.46 (2H, m), 1.95 (3H, br m), 1.66 (1H, m), 1.42 (9H, s),1.04 (1H, m) and 0.83 (6H, m).

STEP K:

S-(1R-{1S-[2-(2-Methoxy-ethoxymethoxy)-ethylcarbamoyl]-2-phenyl-ethylcarbamoyl}-3-methyl-butyl)-pent-4-enoic acid The product from Example 2j(2.5 g, 4 55 mmol) was dissolved in dichloromethane (4 ml) and TFA (4 ml) and stirred for 45 minutes at room temperature. TLC (10% methanol in dichloromethane) indicated that the starting material had been consumed. The solvents were removed in vacuo and the residue was dissolved in ethyl acetate then evaporated to a yellow oil (3.4 g, contained TFA) which was used without further purification. $^1$H—NMR; δ(CDCl$_3$), 8.10 (1H, m), 7.46 (1H, m), 7.29–7.18 (5H, m), 5.68 (1H, m), 4.91 (4H, m), 4.65 (1H, s), 3.76–3.46 (11H, m), 3.02 (2H, m), 2.60 (2H, m), 1.81 (1H, m), 1.62 (1H, m), 1.19–1.09 (2H, m) and 0.84 (7H, m).

STEP L:

3R-{1S-[2-(2-Methoxy-ethoxymethoxy)ethylcarbamoyl]-2-phenyl-ethylcarbamoyl}-5-methyl-2S-propen-2-yl-hexanohydroxamic acid The product from Example 2k(3.4 g, 6.9 mmol) was dissolved in DMF (50 ml) and the solution was cooled to 0° C. during the addition of HOBt (0.93 g, 6.9 mmol) and EDC (1.3 g, 6.9 mmol). The mixture was stirred at 0° C. for ca. 1 hour then at room temperature for ca. 2 hours to ensure complete formation of the active ester. The solution was cooled back to 0° C. and hydroxylamine hydrochloride (0.72 g, 10.3 mmol) was added, followed by NMM (1 ml, 9.1 mmol) and the reaction mixture was allowed to warm to room temperature then stirred for 60 hours. The solvent was removed in vacuo and the residue was triturated with a mixture of diethyl ether (50 ml) and water (25 ml) and left to stand for 2 hours. The resulting oily solid was collected by filtration and further purified by column chromatography (acid-washed silica, gradient elution with 5–10% methanol in dichloromethane). Fractions containing the hydroxamic acid (TLC, red stain with ethanolic $FeCl_3$ solution) were combined and recrystallised twice from methanol-diisopropyl ether. Yield: 140 mg (4%). m.p. 186–188° C.; $^1$H—NMR; $\delta(CD_3OD)$, 8.51 (1H, d, J=8.4 Hz), 7.92 (1H, m), 7.28–7.08 (6H, m), 5.39 (1H, m), 4.82 (2H, m), 4.68 (3H, m), 3.69–3.50 (4H, m), 3.32 (7H, m), 3.06, 2.84 (2H, ABX, J=5.3, 10.2, 13.8 Hz), 2.44 (1H, m), 2.03–1.78 (2H, m), 1.55–1.32 (3H, m), 0.97 (1H, m), 0.85 (3H, d, J=6.5 Hz) and 0.79 (3H, d, J=6.4 Hz). $^{13}$C—NMR; $\delta(CD_3OD)$, 176.3, 173.6, 172.4, 138.5, 136.1, 130.4, 129.5, 127.9, 117.3, 96.6, 73.0, 68.0, 67.4, 59.1, 56.0, 41.6, 40.6, 40.5, 39.0, 27.0, 24.5, and 21.8. Found: C, 61.68, H, 7.85, N, 8.44%; $C_{26}H_{41}N_3O_7$ requires: C, 61.52, H, 8.14, N, 8.28%.

EXAMPLE 3

2S-Allyl-$N^1$-hydroxy-3R-isobutyl-$N^4$-{1S-[2-(2-methoxy-ethoxymethoxy) ethylcarbamoyl]-2,2-dimethyl-propyl)-succinamide

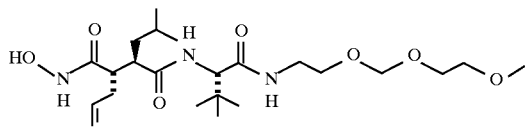

The title compound was prepared according to the methods of Example 2, substituting Cbz-tert-leucine for Cbz-phenylalanine. m.p. 170.5° C. $^1$H—NMR; $\delta(CD_3OD)$, 7.98 (1H, m), 5.57 (1H, m), 4.91 (2H, m), 4.57 (2H, s), 4.20 (1H, d, J=3.7 Hz), 3.58–3.17 (8H, br m), 3.26 (3H, s), 2.61 (1H, m), 2.28–2.09 (2H, m), 2.08–1.94 (1H, m), 1.18–1.15 (2H, m), 1.13 (1H, m), 0.92 (9H, s), 0.78 (3H, d, J=6.3 Hz) and 0.73 (3H, d, J=6.4 Hz). $^{13}$C—NMR; $\delta(CD_3OD)$, 176.4, 172.5, 136.0, 117.5, 96.6, 73.0, 68.0, 67.5, 62.4, 59.1, 48.1, 41.8, 40.3, 36.4, 35.1, 27.3, 27.0, 24.5 and 21.9.

EXAMPLE 4

2S-Allyl-$N^1$-hydroxy-3R-isobutyl-$N^4$-{1S-[2-(2-methoxy-ethoxy)-ethylcarbamoyl]-2,2-dimethyl-propyl}-succinamide

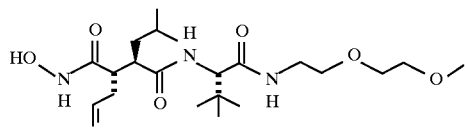

The title compound was prepared according to the method of Example 2, substituting L-tert-leucine-N-2-(2-methoxyethoxy)ethylamide for L-phenylalanine-N -2-(2-methoxy-ethoxymethoxy)ethylamide. m.p. 220°–221 ° C. $^1$H—NMR; $\delta((CD_3)_2SO)$, 8.60 (1H, s), 7.79 (1H, t, J=5.6 Hz), 7.70 (1H, d, J=9.2 Hz), 5.57–5.36 (1H, m), 4.82–4.70 (2H, m), 4.09 (1H, d, J=9.2 Hz), 3.38–3.15 (6H, m), 3.08 (3H, s), 3.11–2.98 (2H, m), 2.61–2.46 (1H, m), 2.20–1.76 (3H, m), 1.31–1.06 (2H, m), 0.89–0.71 (1H, in), 0.78 (9H, s), 0.66 (3H, d, J=6.3 Hz) and 0.60 (3H, d, J=6.4 Hz). $^{13}$C—NMR; $\delta((CD_3)_2SO)$, 173.5, 170.0, 169.3, 135.9, 116.0, 71.2, 69.3, 69.0, 60.1, 58.0, 45.9, 45.8, 42.0, 38.3, 34.9, 33.6, 26.8, 25.3, 24.0 and 21.7. IR; $v_{max}$(KBr), 3287, 2956, 1634, 1556 and 1368 $cm^{-1}$. L-tert-leucine-N-2-(2-methoxyethoxy)ethylamide was prepared as follows.

Potassium phthalimide (20 g, 108 mmol) was suspended in toluene (100 ml) and n-hexadecyl-tri-n-butyl-phosphonium bromide (4.4 g, 8.66 mmol) and 2-methoxyethoxy)ethylbromide (11.5 ml, 84.8 mmol) were added. The reaction mixture was heated at reflux for 2 hours after which TLC analysis revealed only a trace of starting material. The mixture was cooled to room temperature and inorganic residues were removed by filtration and washed with diethyl ether. The combined filtrate and washings were evaporated under reduced pressure and the residue was purified by flash chromatography (silica gel, 40% ethyl acetate in hexane as eluent) to provide 2-(methoxyethoxy) ethylphthalimide as a colourless oil (18.1 g, 67%). $^1$H—NMR; $\delta(CDCl_3)$, 7.82 (2H, m), 7.70 (2H m), 3.91 (2H, t, J=5.8 Hz), 3.73 (2H, t, J=5.8 Hz), 3.63 (2H, m), 3.50 (2H, m) and 3.29 (3H, s).

The phthalimide (9.0 g, 36.1 mmol) was dissolved in dry methanol (500 ml) under argon and hydrazine (1.4 ml, 44.6 mmol) was added. The reaction mixture was stirred for two hours at room temperature after which TLC analysis indicated that all of the starting material had been consumed. 1M Hydrochloric acid (21.6 ml) was added and the reaction mixture was concentrated in vacuo. The residue was stored at 4° C. overnight, 0.1M hydrochloric acid (200 ml) was added and the mixture was filtered. The water was removed under reduced pressure and 5M sodium hydroxide was added to pH 11. The product was extracted into dichloromethane and the combined organic extracts were dried over sodium sulphate, filtered and evaporated to give 2-(methoxyethoxy)ethylamine as a colourless oil (2.84 g, 66%). $^1$H—NMR; $\delta(CDCl_3)$, 3.62 (2H, m), 3.55–3.49 (4H, m), 3.39 (3H, s), 2.85 (2H, t, J=5.8 Hz) and 1.80 (2H, br s).

The amine (2.84 g, 23.9 mmol) was dissolved in DMF (80 ml) and treated with Cbz-L-tert-leucine pentafluorophenyl ester (10.3 g, 23.8 mmol). The reaction mixture was stirred at room temperature for 3 hours, and the solvent was removed under reduced pressure. The residue was dissolved in ethyl acetate and the solution was washed successively with water, 1M sodium carbonate (x2), 1M hydrochloric acid and water (x3). The organic phase was dried over sodium sulphate, filtered and evaporated under reduced pressure. The residue was purified by flash chromatography (silica, ethyl acetate as solvent) to provide Cbz-L-tert-leucine-N-2-(2-methoxyethoxy)ethylamide as a colourless oil (7.7 g, 88%). $^1$H—NMR; $\delta(CDCl_3)$, 7.33 (5H, m), 6.39 (1H, m), 5.62 (1H, d, J=9.3 Hz), 5.07 (2H, dd, J =12.2, 2.6 Hz), 390 (1H, d, J=9.4 Hz), 3.60–3.49 (8H, m), 3.37 (3H, s) and 0.98 (9H, s).

Cbz-L-tert-leucine-N-2-(2-methoxyethoxy)ethylamide (7.66 g, 20.9 mmol) was dissolved in ethanol (100 ml) under an argon atmosphere and 10% Palladium on charcoal (1 g) was added as a slurry in ethanol (30 ml). The mixture was placed under an atmosphere of hydrogen as and left to stir overnight at room temperature. TLC analysis revealed that no starting material remained. The flask was purged with argon and the catalyst was removed by filtration. The solvent was removed under reduced pressure to provide L-tert-leucine-N-2-(2-methoxyethoxy)ethylamide as a colourless oil (4.55 g, 94%). $^1$H—NMR; $\delta(CDCl_3)$, 6.95 (1H, br s), 3.60–3.40 (8H, m), 3.34 (1H, s), 3.01 (1H, s), 1.61 (2H, br s) and 0.95 (9H, s).

The compounds of Examples 5–7 were prepared by a procedure analogous to that of Example 2, utilising the appropriate L-tert-leucine derivative in lieu of L-phenylalanine-N-2-(2-methoxy-ethoxymethoxy) ethylamide. The required L-tert -leucine derivatives were prepared by procedures analogous to that described above for L-tert-leucine-N-2-(2-methoxyethoxy)ethylamide.

EXAMPLE 5

2S-Allyl-N¹-hydroxy-3R-isobutyl-N⁴-(1S-2-[2-(2-methoxy-ethoxy)-ethoxy]-ethylcarbamoyl]-2,2-dimethyl-propyl}-succinamide

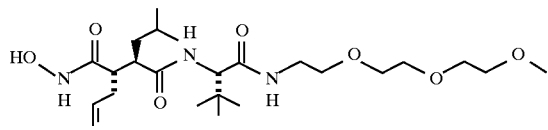

m.p. 208–209° C. ¹H—NMR; δ(CD₃OD), 8.07–8.00 (1H, m), 7.94 (1H, d, J=9.2 Hz), 5.67–5.49 (1H, m), 4.97-4.83 (2H, m), 4.21 (1H, d, J=9.1 Hz), 3.57–3.37 (9H, m), 3.33–3.12 (6H, s and m), 2.68–2.53 (1H, m), 2.30–1.96 (3H, m), 1.49–1.19 (2H, m), 1.06–0.90 (1H, m), 0.93 (9H, s), 0.78 (3H, d, J=6.5 Hz) and 0.73 (3H, d, J=6.5 Hz). ¹³C—NMR; δ(CD₃OD), 173.5, 170.0, 169.3, 135.9, 116.0, 71.3, 69.7, 69.6, 69.0, 60.1, 58.0, 45.9, 45.8, 34.9, 33.6, 26.8, 25.3, 24.0 and 21.7. IR; $v_{max}$(KBr), 3284, 2955, 1624, 1549 and 1102 cm⁻¹. Found: C 57.80, H 9.15, N 8.54%; $C_{24}H_{45}N_3O_7$. 0.6 H₂O requires: C 57.83, H 9.34, N 8.43%.

EXAMPLE 6

2S-Allyl-N⁴-{1S-[2,2-di-(methoxymethyl)-propylcarbamoyl}-2,2-dimethyl-propyl]-N¹-hydroxy-3R-isobutyl-succinamide

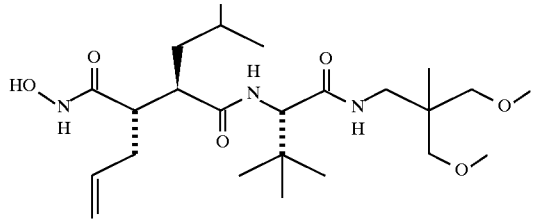

m.p. 212°–214° C. ¹H—NMR; δ((CD₃)₂SO), 8.61 (1H, s), 7.74 (1H, d, J=9.1 Hz), 7.48 (1H, m), 5.46 (1H, m), 4.82-4.68 (2H, m), 4.15 (1H, d, J=9.1 Hz), 3.06 (6H, s), 3.11–3.07 (5H, m), 2.76 (1H, m), 2.55 (1H, m), 2.20–1.93 (2H, m), 1.84 (1H, m), 1.33–1.07 (2H, m), 0.80 (1H, m), 0.78 (9H, s), 0.65 (3H, d, J=6.4 Hz), 0.61 (3H, s) and 0.59 (3H, d, J=6.8 Hz). ¹³C—NMR; δ((CD₃)₂SO), 173.5, 170.4, 169.3, 135.9, 116.0, 75.5, 60.3, 58.7, 45.8, 42.1, 34.9, 33.7, 26.8, 25.3, 24.1, 21.6 and 17.6. IR; $v_{max}$(KBr), 3277, 2955, 1634, 1538, 1385 and 1114 cm⁻¹.

EXAMPLE 7

2S-Allyl-N⁴-{1S-[2,2-di-(methoxymethyl)-butylcarbamoyl}-2,2-dimethyl-propyl)N¹-hydroxy-3R-isobutyl-succinamide

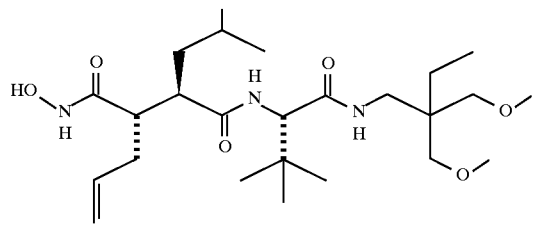

m.p. 225–226° C. ¹H—NMR; δ((CD₃)₂SO), 8.61 (1H, s), 7.74 (1H, d, J=9.1 Hz), 7.34–7.25 (1H, m), 5.57–5.38 (1H, m), 4.82-4.69 (2H, m), 4.17 (1H, d, J=9.0 Hz), 3.07 (6H, s), 3.13–2.90 (5H, m), 2.83–2.70 (1H, m), 2.61–2.48 (1H, m), 2.21–1.93 (2H, m), 1.90–1.78 (1H, m), 1.34–1.10 (6H, m), 0.79 (9H, s), 0.66–0.60 (9H, m). ¹³C—NMR; δ((CD₃)₂SO), 173.5, 170.4, 169.3, 135.9, 116.0, 73.3, 60.2, 58.6, 45.8, 42.1, 34.9, 33.7, 26.8, 25.3, 24.1, 22.8, 21.6 and 7.5. IR; $v_{max}$(KBr), 3268, 2960, 1633, 1531, 1369 and 1109 cm⁻¹.

EXAMPLE 8

N⁴-Hydroxy-2R-isobutyl-N¹-{1S-[2-(2-methoxy-ethoxy)-ethylcarbamoyl]-2,2-dimethyl -propyl}3S-(thiophen-2-yl-sulfanylmethyl)-succinamide

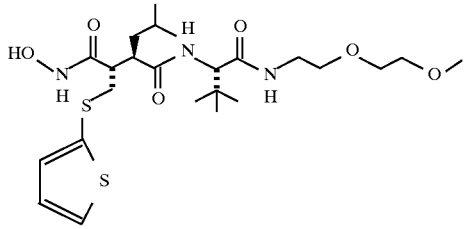

STEP A:
2-(1R-{1S-[2-(2-Methoxy-ethoxy)-ethylcarbamoyl]-2,2-dimethyl-propylcarbamoyl-3methyl-butyl)-malonic acid dibenzyl ester 2-Benzyloxycarbonyl-3R-isobutyl-succinic acid-4-benzyl ester (prepared as described in WO 90/05719) (5.9 g, 16.1 mmol) was dissolved in DMF (100 ml) and the solution was cooled to 0° C. during the addition of HOBt (2.6 g, 19.3 mmol) followed by EDC (3.7 g, 19.3 mmol). The reaction mixture was warmed to room temperature and stirred for 3.5 hours. L-tert-leucine-N-2-(2-methoxyethoxy)ethylamide (3.72 g, 16.0 mmol) was added and the reaction mixture was stirred at room temperature for 3 days. The solvent was removed under reduced pressure and the residue was dissolved in ethyl acetate (200 ml). The solution was washed successively with water (x2), 1M hydrochloric acid, 1M sodium carbonate and finally with water, dried over sodium sulphate, filtered and concentrated under reduced pressure. The residue was purified by flash chromatography (silica gel, 70% ethyl acetate in hexane as eluent) to give the title compound as a colourless oil (8.08 g, 86%). ¹H—NMR; δ(CDCl₃), 7.31 (10H, m), 6.51 (1H, d, J=9.2 Hz), 6.16 (1H, m), 5.16–5.06 (2H, dd, J=13.5, 12.1 Hz), 5.10 (2H, s), 4.13 (1H, d, J=9.1 Hz), 3.84 (1H, d, J=10.1 Hz), 3.61–3.41 (8H, m), 3.40 (3H, s), 3.00 (1H, ddd, J=3.9, 3.9, 10.4 Hz), 1.65–1.56 (2H, m), 1.06–1.00 (1H, m), 0.97 (9H, s), 0.80 (3H, d, J=6.6 Hz) and 0.77 (3H, d, J=6.6 Hz).
STEP B:
2-(1R-{1S-[2-(2-Methoxy-ethoxy)-ethylcarbamoyl)-2,2-dimethyl-propylcarbamoyl}3-methyl-butyl)-acrylic acid
2-(1R-{1S-[2-(2-Methoxy-ethoxy)-ethylcarbamoyl]-2,2-dimethyl-propylcarbamoyl}-3-methyl-butyl)-malonic acid dibenzyl ester (8.08g, 13.9 mmol) was dissolved in ethanol (150 ml) and 10% palladium on charcoal (1.6 g) was added. Hydrogen gas was passed through the suspension with vigorous stirring for 5.5 hours. The system was purged with argon and the catalyst was removed by filtration. The filtrate, containing 2-(1R-{1S-[2-(2-methoxy-ethoxy)-ethylcarbamoyl]-2,2-dimethyl -propylcarbamoyl}3-methyl-butyl)-malonic acid, was cooled to 0° C. and piperidine (1.5 ml, 15.2 mmol) was added, followed by 37% aqueous formaldehyde solution (10 ml), dropwise. The reaction mixture was allowed to warm to room temperature and stirred at room temperature overnight. The solvent was removed under reduced pressure, the residue was dissolved in ethyl acetate and extracted with 1M sodium carbonate (3×50 ml). The aqueous extracts were combined and acidified with conc. hydrochloric acid before extraction into ethyl acetate. The organic layers were combined, dried over sodium sulphate, filtered and evaporated. The residue was crystallised from DIPE to give the title compound as a white solid (4.4 g, 79% overall). $^1$H—NMR; $\delta$(CDCl$_3$), 8.24 (1H, d, J=9.8 Hz), 7.00 (1H, br s), 6.45 (1H, s), 6.03 (1H, s), 4.43 (1H, d, J=9.8 Hz), 4.02 (1H, m), 3.67–3.44 (8H, m), 3.41 (3H, s), 1.80–1.70 (1H, m), 1.55–1.47 (2H, m), 0.89 (9H, s) and 0.87 (6H, d, J=6.2 Hz).

STEP C:

3R-{1S-[2-(2-Methoxy-ethoxy)-ethylcarbamoyl]-2,2-dimethyl-propylcarbamoyl}-5-methyl-2S-(thiophen-2-ylsulfanylmethyl)-hexanoic acid 2-(1R-{1S-[2-(2-Methoxy-ethoxy)-ethylcarbamoyl]-2,2-dimethyl-propylcarbamoyl}-3-methyl-butyl)-acrylic acid (4.4 g, 11.0 mmol) was dissolved in methanol (100 ml) and placed under an argon atmosphere. Thiophene-2-thiol (3 g, 25.9 mmol) was added and the reaction mixture was stirred at 60° C. in the dark overnight. The solvent was removed in vacuo and DIPE was added to the residual oil, whereupon a white solid precipitated. The solid was collected, washed thoroughly with DIPE and dried. IH NMR analysis revealed that the reaction was incomplete. The mixture of starting material and product were redissolved in methanol and the reaction was repeated as described above. The solvent was removed under reduced pressure and the residue was crystallised from diethyl ether and recrystallised from ethyl acetate to give the title compound as a white solid (2.91 g, 51%). $^1$H—NMR; $\delta$(CDCl$_3$), 7.83 (1H, m), 7.78 (1H, d, J=8.9 Hz), 7.45 (1H, d, J=4.2 Hz), 6.95 (1H, m), 6.88 (1H, m), 4.02 (1H, d, J=9.2 Hz), 3.33–3.17(7H, m), 3.08 (3H, s), 3.05–3.00 (2H, m), 2.67–2.60 (2H, m), 2.42 (1H, m), 1.39–1.06 (2H, m), 0.82 (1H, m), 0.74 (9H, s), 0–64 (3H, d, J=6.5 Hz) and 0.59 (3H, d, J=6.5 Hz).

STEP D:

N$^4$-Hydroxy-2R-isobutyl-N$^1$-{1S-[2-(2-methoxy-ethoxy)-ethylcarbamoyl]-2,2-dimethyl -propyl}3S-(thiophen-2-yl-sulfanylmethyl)-succinamide 3R-{1S-[2-(2-Methoxy-ethoxy)-ethylcarbamoyl]-2,2-dimethyl-propylcarbamoyl}-5-methyl-2S-(thiophen-2-ylsulfanylmethyl)-hexanoic acid (2.91 g, XX mmol) was converted to the title compound (1.00 g, 33%) by a method analogous to that described in Example 2 (Step L). m.p. 198–199° C. $^1$H—NMR; $\delta$(CD$_3$OD), 8.85 (1H, m), 7.87–7.73 (2H, m), 7.42 (1H, m), 6.95 (1H, m), 6.85 (1H, m), 4.04 (1H, d, J=10.0 Hz), 3.38–3.13 (7H, m), 3.08 (3H, s), 3.10–2.84 (2H, m), 2.63–2.49 (2H, m), 2.28 (1H, m), 1.30 (1H, m), 1.09 (1H, m), 0.78 (1H, m), 0.73 (9H, s), 0.64 (3H, d, J=6.4 Hz) and 0.59 (3H, d, J=6.5 Hz). $^{13}$C—NMR; $\delta$(CD$_3$OD), 172.8, 169.9, 167.9, 133.9, 132.5, 129.5, 127.7, 71.2, 69.3, 69.0, 60.1, 58.0, 46.0, 33.6, 26.8, 25.3, 23.9 and 21.6. IR; $\nu_{max}$(KBr), 3287, 2955, 1634, and 1556 cm$^{-1}$.

Found: C 54.06, H 7.78, N 7.86%; C$_{24}$H$_{41}$N$_3$O$_6$S$_2$. 0.1 H$_2$O requires: C 54.03, H 7.78, N 7.88%.

The compounds of Examples 9 and 10 were prepared by a procedure analogous to that described in Example 8, utilising the appropriate L-tert-leucine derivative in lieu of L-tert-leucine-N-2-(2-methoxyethoxy)ethylamide. The required L-tert-leucine derivatives were prepared by procedures analogous to that described above (Example 4) for L-tert-leucine-N-2-(2-methoxyethoxy)ethylamide.

EXAMPLE 9

N$^4$-Hydroxy-2R-isobutyl-N$^1$-(1S{2-[2-(2-methoxy-ethoxy)-ethoxy]-ethylcarbamoyl}-2,2-dimethyl-propyl)-3S-(thiophen-2-yl-sulfanylmethyl)-succinamide

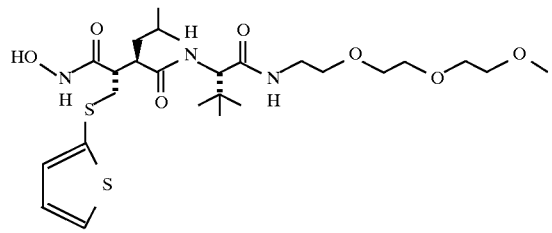

m.p. 167–168° C. $^1$H—NMR; $\delta$((CD$_3$)$_2$SO), 8.79 (1H, d, J=1.7 Hz), 7.86–7.72 (2H, m), 7.44 (1H, m), 6.94 (1H, m), 6.85 (1H, m), 4.04 (1H, d, J=9.3 Hz), 3.41–3.14 (10H, m), 3.09 (3H, s), 3.10–2.85 (3H, m), 2.63–2.50 (2H, m), 2.23 (1H, m), 1.39–1.02 (2H, m), 0.89–0.60 (10H, s and m), 0.63 (3H, d, J=6.5 Hz) and 0.59 (3H, d, J=6.5 Hz). $^{13}$C —NMR; $\delta$((CD$_3$)$_2$SO), 172.7, 169.9, 167.9, 133.8, 132.5, 129.5, 127.8, 71.3, 69.7, 69.6, 69.5, 68.9, 60.1, 58.0, 45.9, 33.6, 26.8, 25.3, 24.0 and 21.6. IR; $\nu_{max}$(KBr), 3285, 2955, 1636, 1549 and 1103 cm$_{-1}$. Found: C 54.02, H 7.88, N 7.29%; C$_{26}$H$_{45}$N$_3$O$_7$S$_2$. 0.1 H20 requires: C 54.07, H 7.89, N 7.28%.

EXAMPLE 10

N$^1$-{1S-[2,2-Di-(methoxymethyl)-propylcarbamoyl]-2,2-dimethyl-propyl}N$^4$-hydroxy -3R-isobutyl-3S-(thiophen-2-yl-sulfanylmethyl)-succinamide

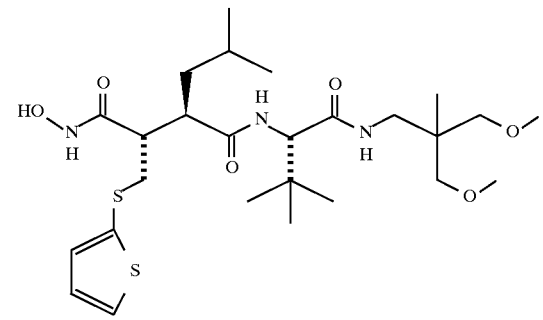

m.p. 207–209° C. $^1$H—NMR; $\delta$((CD$_3$)$_2$SO), 8.79 (1H, s), 7.79 (1H, d, J=9.1 Hz), 7.48 (1H, t, J=6.2 Hz), 7.44 (1H, m), 6.96 (1H, m), 6.88 (1H, m), 4.11 (1H, d, J=9.1 Hz), 3.11–2.87 (12H, s and m), 2.76 (1H, m), 2.65–2.51 (2H, m), 2.25 (1H, m), 1.31 (1H, m), 1.12 (1H, m), 0.88–0.70 (10H, s and m), 0.63 (3H, d, J=6.4 Hz), 0.60 (3H, s) and 0.59 (3H, d, J=6.3 Hz). $^{13}$C—NMR; $\delta$((CD$_3$)$_2$SO), 172.8, 170.3, 167.9, 133.8, 132.6, 129.5, 127.8, 75.5, 60.1, 58.6, 46.0, 45.8, 42.1, 40.5, 33.6, 26.8, 25.2, 24.0, 21.6 and 17.5. IR; $\nu_{max}$(KBr), 3192, 2958, 1637, 1533 and 1369 cm$^{-1}$.

EXAMPLE 11

N⁴-Hydroxy-2R-isobutyl-N¹-{1S-[2-(2-methoxy-ethoxy)-ethylcarbamoyl]-2,2-dimethyl -propyl}-3S-propyl-succinamide

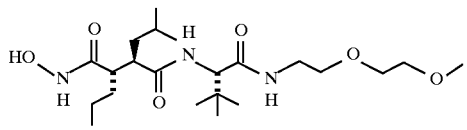

2S-Allyl-N¹-hydroxy-3R-isobutyl-N⁴-{1S-[2-(2-methoxy-ethoxy)-ethylcarbamoyl]-2,2-dimethyl-propyl}-succinamide (example 4, 400 mg, 0.9 mmol) was dissolved in ethanol (40 ml) The solution was placed under an argon atmosphere and 10% palladium on charcoal (50 mg) was added. Hydrogen gas was bubbled through the solution for 3 hours with vigorous stirring. The catalyst was removed by filtration and the filtrate was concentrated under reduced pressure. The residue was purified by flash chromatography (acid-washed silica, 5% methanol in dichloromethane as eluent) to provide the title compound as a white solid (300 mg, 70%). m.p. 250°–253° C. ¹H—NMR; δ((CD₃)₂SO), 10.32 (1H, s), 8.61 (1H, s), 7.76 (1H, t, J=5.6 Hz), 7.66 (1H, d, J=9.3 Hz), 4.08 (1H, d, J=9.3 Hz), 3.38–3.15 (6H, m), 3.10–2.94 (5H, s and m), 2.51 (1H, m), 1.92 (1H, m), 1.43–0.89 (7H, m), 0.77 (9H, s), 0.65 (3H, d, J=6.3 Hz), 0.59 (3H, d, J=6.4 Hz) and 0.71–0.55 (3H, m). ¹³C—NMR; δ((CD₃)₂SO) 173.7, 170.1, 71.2, 69.3, 69.0, 60.1, 58.0, 46.2, 45.8, 33.6, 32.8, 26.8, 25.4, 24.0, 21.7, 20.0 and 13.9. IR; $v_{max}$(KBr), 3282, 2956, 1634, 1537, 1367 and 1106 cm⁻¹.

EXAMPLE 12

The following table illustrates the increase in water solubility of the compounds of the present invention over similar compounds known in the art where $R_4$=Me (comparators 1 to 3), while maintaining in vitro actvity against MMPs.

Comparator 1: N⁴-(2,2-Dimethyl-1S-methylcarbamoyl-propyl)-2S, N¹-dihydroxy-3R -isobutyl-succinamide Comparator 2: 2S-Allyl-N⁴-(2,2-Dimethyl-1S-methylcarbamoyl-propyl)-N⁴-hydroxy -3R-isobutyl-succinamide Comparator 3: N¹-(2,2-Dimethyl-1S-methylcarbamoyl-propyl)-N⁴-hydroxy-2R -isobutyl-3-(thiophen-2-yl-sulfanylmethyl)-succinamide

| TEST COMPOUND | HFC† IC₅₀ (nM) | Getatinase A IC₅₀ (nM) | Stromelysin-1 IC₅₀ (nM) | Aq. solubility (mg/ml) |
|---|---|---|---|---|
| Example 1 | 10 | 15 | 60 | ≧29.6 |
| Comparator 1 | 5 | 6 | 200 | 7.7 |
| Example 4 | 1 | 7 | 40 | 4.7 |
| Example 6 | 20 | 30 | 50 | 0.4 |
| Comparator 2 | 4 | 15 | 80 | 0.04 |
| Example 9 | 2 | 9 | 10 | 0.4 |
| Comparator 3 | 1 | 20 | 40 | 0.18 |

†Human fibroblast collagenase

We claim:
1. A compound of general formula (I)

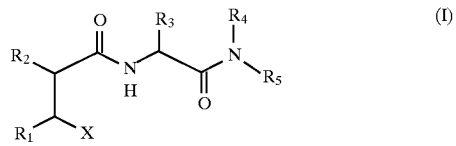

wherein

X is a —CO₂H or —CONHOH group;

$R_1$ is hydrogen, a $C_1$–$C_6$ alkyl, $C_2$–$C_6$ alkenyl, phenyl, substituted phenyl, phenyl($C_1$–$C_6$ alkyl), heterocyclyl, substituted heterocyclyl, heterocyclyl($C_1$–$C_6$ alkyl), substituted heterocyclyl($C_1$–$C_6$ alkyl), or a group BSO$_n$A— wherein n is 0,1 or 2 and B is hydrogen or a ($C_1$–$C_6$) alkyl, phenyl, substituted phenyl, heterocyclyl, $C_1$–$C_6$ acyl, phenacyl or substituted phenacyl group, and A represents $C_1$–$C_6$ alkyl; amino; protected amino; acylamino; OH; SH; $C_1$–$C_6$ alkoxy; $C_1$–$C_6$ alkylamino; $C_1$–$C_6$ alkylthio; aryl($C_1$–$C_6$ alkyl); amino($C_1$–$C_6$ alkyl); hydroxy($C_1$–$C_6$ alkyl), mercapto ($C_1$–$C_6$ alkyl) or carboxy($C_1$–$C_6$ alkyl) wherein the amino-, hydroxy-, mercapto- or carboxyl-group are optionally protected or the carboxyl- group amidated; or lower alkyl substituted by maleimido, succinimido, naphthalimido, 2,3-dihydro-1,3-dioxo-1 H-benz isoquinol -2-yl, carbamoyl, mono(lower alkyl)carbamoyl, di(lower alkyl)carbamoyl, di(lower alkyl)amino, carboxy-lower alkanoylamino, pyrrolidino or morpholino;

$R_2$ is a $C_1$–$C_{12}$ alkyl, $C_2$–$C_{12}$ alkenyl, $C_2$–$C_{12}$ alkynyl, benzyl, cycloalkyl($C_1$–$C_6$ alkyl)-, cycloalkenyl($C_1$–$C_6$ alkyl)-, phenyl($C_1$–$C_6$ alkyl)O($C_1$–$C_6$ alkyl)-, or heteroaryl($C_1$–$C_6$ alkyl)O($C_1$–$C_6$ alkyl)- group, any one of which may be optionally substituted by $C_1$–$C_6$ alkyl, $C_1$–$C_6$ alkoxy, halo or cyano (—CN);

$R_3$ is the side chain of a naturally occurring amino acid, which may be protected if functional groups are present, eg by acylation of amino groups and amidation of carboxyl groups; or a group —CR₆R₇R₈ in which each of $R_6$, $R_7$ and $R_8$ is independently hydrogen, ($C_1$–$C_6$)alkyl, ($C_2$–$C_6$)alkenyl, ($C_2$–$C_6$)alkynyl, phenyl ($C_1$–$C_6$) alkyl, halogen, —CN, —CO₂H, ($C_1$–$C_4$) perfluoroalkyl, —CO₂($C_1$–$C_6$)alkyl, or a group phenyl or heteroaryl which is optionally substituted by one or more substituents independently selected from hydroxyl, halogen, —CN, —CO₂H, —CO₂($C_1$–$C_6$) alkyl, —CONH₂, —CONH($C_1$–$C_6$)alkyl, —CONH ($C_1$–$C_6$alkyl)₂, —CHO, —CH₂OH, ($C_1$–$C_4$) perfluoroalkyl, —O($C_1$–$C_6$)alkyl, —S($C_1$–$C_6$)alkyl, —SO($C_1$–$C_6$)alkyl, —SO₂($C_1$–$C_6$)alkyl, —NO₂, NH₂, —NH($C_1$–$C_6$)alkyl, —N(($C_1$–$C_6$)alkyl)₂, —NHCO ($C_1$–$C_6$)alkyl, ($C_1$–$C_6$)alkyl, ($C_2$–$C_6$) alkenyl, ($C_2$–$C_6$) alkynyl, ($C_3$–$C_8$)cycloalkyl, ($C_4$–$C_8$)cycloalkenyl, phenyl or benzyl; or $R_6$ and $R_7$ together with the carbon atom to which they are attached form a 3 to 8 membered cycloalkyl or a 5- to 6-membered heterocyclic ring; or $R_6$, $R_7$ and $R_8$ together with the carbon atom to which they are attached form a bicyclic ring (for example adamantyl);

$R_4$ is a group of formula —(Z—O)$_n$—Z wherein Z is straight or branched $C_{1-6}$ alkyl optionally interrupted by one or more non-adjacent S and/or N atoms, n is an integer >1, and no continuous linear sequence of atoms in the group $R_4$ is >12, or a straight or branched $C_2$ 6alkyl group, optionally interrupted by one or more non-adjacent S and/or N atoms, which group is substituted by at least two substituents of formula —$(Z)_p$—$(OZ)_q$ wherein Z is straight or branched $C_{1-6}$ alkyl optionally interrupted by one or more non-adjacent S and/or N atoms, p is 1, q is 1 or 2, and no continuous linear sequence of atoms in the group $R_4$ is >12;

$R_5$ is hydrogen or a $(C_1-C_6)$alkyl group;

or a salt, hydrate or solvate thereof.

2. A compound as claimed in claim 1 wherein the stereochemistry is as follows:

C atom carrying the $R_1$ and X groups-S,

C atom carrying the $R_2$ group-R,

C atom carrying the $R_3$ group-S.

3. A compound as claimed in claim 2 wherein $R_1$ is hydrogen, hydroxyl, n-propyl or allyl.

4. A compound as claimed in claim 2 wherein $R_2$ is iso-butyl, n-pentyl, n-hexyl, n-heptyl, n-nonyl, n-decyl, or benzyloxypropyl.

5. A compound as claimed in claim 2 wherein $R_3$ is benzyl, iso-butyl, t-butyl, or 1-fluoro-1-methylethyl.

6. A compound as claimed in claim 2 wherein $R_4$ is 2-(2-methoxyethoxymethoxy) ethyl, 1,1-dimethyl-2-(2-methoxyethoxymethoxy)ethyl, 2-(2-ethoxyethoxymethoxy) ethyl, 2-( 2-(2-methoxyethoxy) ethoxy)ethyl , 2-(2-(3-methoxypropoxy) ethoxy)ethyl, 3-(2-methoxyethoxymethoxy)propyl, 2,2-dimethyl-3-(2-methoxyethoxymethoxy)propyl, 2-(2-ethoxyethoxy)ethyl, 3-(2-methoxyethoxy)propyl, 2,2-di(2-methoxymethyl) propyl, and 2,2-di(2-methoxymethyl)butyl.

7. A compound as claimed claim 2 wherein $R_4$ is 2-(2-methoxyethoxy) ethyl.

8. A compound as claimed in claim 2 wherein $R_5$ is hydrogen.

9. 2S-Allyl-$N^1$-hydroxy-3R-isobutyl-$N^4$-{1S-[2-(2-methoxy-ethoxy) -ethylcarbamoyl]-2,2-dimethyl-propyl}-succinamide, and salts, solvates or hydrates thereof.

10. A compound selected from the group consisiting of:

2S, $N_1$-Dihydroxy-3R-isobutyl-$N_4$-{1S-[2-(2-methoxy-ethoxymethoxy)ethylcarbamoyl]-2,2-dimethyl-propyl}-succinamide, 2S-Allyl-$N_1$-hydroxy-3R-isobutyl-$N^4$-{1S-[2-(2-methoxy -ethoxymethoxy)ethylcarbamoyl]-2-phenyl-ethyl}-succinamide, 2S-Allyl-$N^1$-hydroxy-3R-isobutyl-$N^4$-{ 1S-[2-(2-methoxy-ethoxymethoxy) ethycarbamoyli]-2,2-dimethyl-propyl}-succinamide, 2S-Allyl-$N^1$-hydroxy- 3R-isobutyl -$N^4$-(1S-2-[2-(2-methoxy-ethoxy)-ethoxy]-ethylcarbamoyl]-2,2-dimethyl-propyl}succinamide, 2S-Allyl-$N^4$-{1S-[2,2-di-(methoxymethyl)-propylcarbamoyl}-2,2-dimethyl-propyl]-$N^1$-hydroxy-3R-isobutyl-succinamide, 2S-Allyl-N-1S-[2,2-di-(methoxymethyl)-butylcarbamoyl]-2,2-dimethyl-propyl-}$N^1$-hydroxy-3R-isobutyl-succinamide), $N^4$-Hydroxy-2R-isobutyl- $N^1$-{1S-[2-( 2-methoxy-ethoxy)-ethylcarbamoyl]-2,2-dimethyl -propyl}-3S-(thiophen-2-yl-sulfanylmethyl)-succinamide), $N^4$-Hydroxy-2R- isobutyl- $N^1$ -(1S-{2-[2-(2-methoxy-ethoxy)-ethoxy]-ethylcarbamoyl}-2,2-dimethyl-propyl)-3S-(thiophen-2-yl-sulfanylmethyl)-succinamide), $N^1$-{1S-[2,2-Di -(methoxymethyl)-opropycarbamoyl]-2, 2-dimethyl-propyl}-$N^4$-hydroxy -3R-isobutyl-3S-(thiophen-2-yl-sulfanylmethyl)-succinamide, $N^4$-Hydroxy-2R-isobutyl-$N^1$-{1S-[2-(2-methoxy-ethoxy) -ethylcarbamoyl]-2,2-dimethyl -propyl}-3S-propyl-succinamide), and salts, solvates or hydrates thereof.

11. A pharmaceutical or veterinary composition comprising a compound as claimed in claim 1, together with a pharmaceutically or veterinarily acceptable carrier.

12. A composition as claimed in claim 11 which is adapted for oral administration.

13. A composition as claimed in claim 11 in which the said compound is in aqueous solution.

* * * * *